(12) United States Patent
Richter

(10) Patent No.: US 7,052,510 B1
(45) Date of Patent: May 30, 2006

(54) TWO BALLOON STAGED STENT EXPANSION

(75) Inventor: Jacob Richter, Ramat Hasharon (IL)

(73) Assignee: Medinol, Ltd., Tel-Aviv (IL)

( * ) Notice: Subject to any disclaimer, the term of this patent is extended or adjusted under 35 U.S.C. 154(b) by 834 days.

(21) Appl. No.: 09/878,749

(22) Filed: Jun. 11, 2001

Related U.S. Application Data

(60) Provisional application No. 60/211,642, filed on Jun. 14, 2000.

(51) Int. Cl.
  *A61F 2/06* (2006.01)
(52) U.S. Cl. .................. 623/1.11; 604/101.01; 604/101.02
(58) Field of Classification Search ........... 604/101.02, 604/101.01, 108; 623/1.23, 1.11
See application file for complete search history.

(56) References Cited

U.S. PATENT DOCUMENTS

| | | | |
|---|---|---|---|
| 4,744,366 A * | 5/1988 | Jang .................. 606/194 |
| 5,342,305 A * | 8/1994 | Shonk ............... 604/101.02 |
| 5,358,487 A * | 10/1994 | Miller ................ 604/103.11 |
| 5,447,497 A | 9/1995 | Sogard et al. |
| 5,653,689 A | 8/1997 | Buelna et al. |
| 5,704,913 A * | 1/1998 | Abele et al. ......... 604/101.02 |
| 5,876,376 A | 3/1999 | Schwab et al. |
| 6,136,011 A * | 10/2000 | Stambaugh ............ 606/159 |
| 6,419,685 B1 * | 7/2002 | Di Caprio et al. ....... 606/192 |
| 6,605,056 B1 * | 8/2003 | Eidenschink et al. .... 604/96.01 |

FOREIGN PATENT DOCUMENTS

| | | |
|---|---|---|
| EP | 0 903 121 A1 | 3/1999 |
| WO | 96/38109 | 12/1996 |
| WO | 99/12601 | 3/1999 |
| WO | 00/03662 | 1/2000 |

OTHER PUBLICATIONS

International Search Report for International Application No. PCT/IL01/00543.

\* cited by examiner

*Primary Examiner*—Glenn K. Dawson
*Assistant Examiner*—Darwin P Erezo
(74) *Attorney, Agent, or Firm*—Morgan & Finnegan, LLP

(57) ABSTRACT

A catheter with two balloons for implanting a stent without flaring at the ends of the stent during implantation has an outer balloon overlying an inner balloon. The length of the inner balloon is shorter than the length of the outer balloon and shorter than a stent which is mounted over both balloons. Upon inflation of the inner balloon, the inner balloon expands only the center of the stent. After the center of the stent is expanded, further application of pressure bursts the inner balloon allowing application of pressure to the outer balloon. The outer balloon is then inflated, expanding the ends of the stent.

23 Claims, 3 Drawing Sheets

TWO BALLOON STAGED STENT EXPANSION

This application claims the benefit of Provisional Application No. 60/211,642, filed Jun. 14, 2000.

FIELD OF THE INVENTION

The present invention relates generally to catheter balloons for implanting stents. More particularly, the present invention relates to a catheter balloon which utilizes two balloons coaxially disposed within one another.

BACKGROUND OF THE INVENTION

It is well known td use a balloon catheter to intraluminally deliver and implant a stent. Typically, to implant a stent with a balloon catheter, the unexpanded stent is disposed around the deflated balloon of a balloon catheter. The balloon is then delivered to the desired implantation site and inflated. The inflation of the balloon expands the stent, implanting it at the desired location.

One shortcoming of conventional balloon catheters is that they may cause the ends of the stent to flare out during implantation. This flaring out is referred to as "dogboning". Dogboning causes at least two undesirable effects. First, dogboning exacerbates any foreshortening of the stent during expansion. Second, dogboning causes the edges of the end of the stent to project in a direction perpendicular to the wall of the vessel in which the stent is being implanted. These projecting edges potentially increase trauma to the wall of the lumen.

SUMMARY OF THE INVENTION

Embodiments of the present invention include a balloon catheter with two balloons is disclosed. An inner balloon is shorter than an outer balloon, and also shorter than a stent which is to be implanted. The outer balloon overlays the inner balloon, and is longer that the stent.

To implant the stent, the catheter is delivered to a desired site in a vessel. Pressure is applied to the inner balloon, inflating the balloon and implanting the central portion of the stent. Further increases in pressure rupture the inner balloon. Because the outer balloon overlays the inner balloon, the pressure inflates the outer balloon, expanding the remainder of the stent. The balloons may then be deflated and removed, leaving the implanted stent in the vessel.

DETAILED DESCRIPTION OF THE INVENTION

Figure 1:
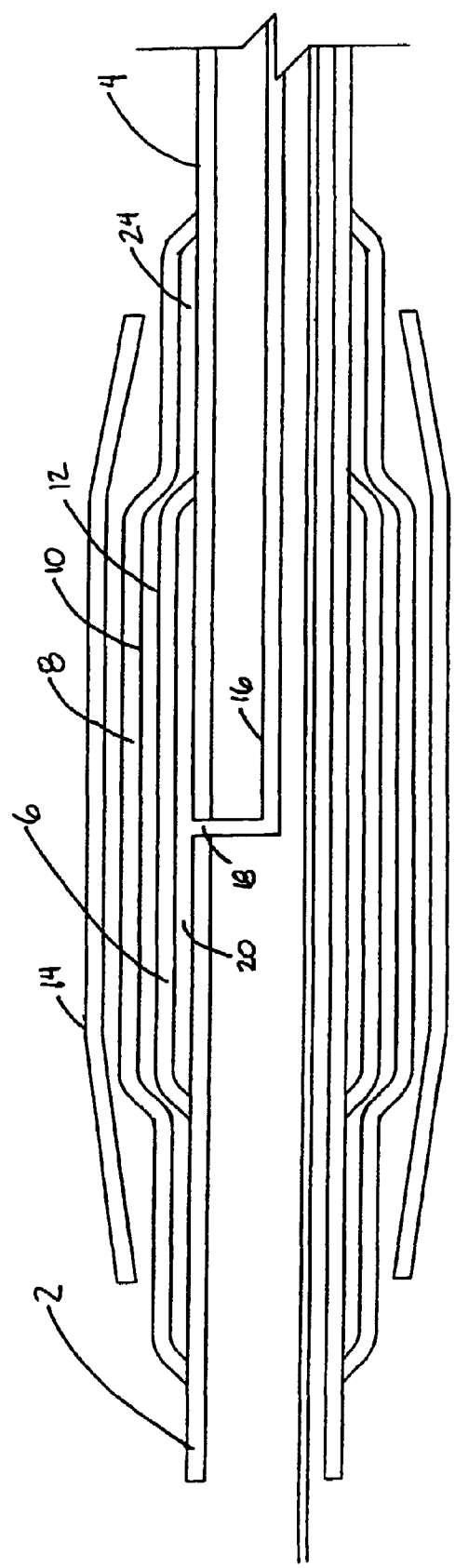
FIG. 1 shows a cross-sectional view of an embodiment of a catheter balloon assembly constructed according to the principles of the present invention which is in the deflated condition.

FIG. 1 shows a schematic view of an embodiment of a catheter balloon constructed in accordance with the principles of the present invention. The details of the catheter have not been included here, as they are well known to those skilled in the art. The precise configurations of the catheter shaft, guidewire lumen, and inflation lumen can be chosen as desired. For example, the catheter may be designed as a rapid-exchange system or as an over-the-wire system. The balloon catheter includes a catheter shaft 2. An inner balloon 6 is sealed to the outer surface 4 of the catheter shaft 2. The length of the inner balloon is chosen so that it is less than the length of the stent which it is designed to implant. The inner balloon 6 may be formed of a non-compliant material.

An outer balloon 8 is disposed around the inner balloon 6. The inner surface 10 of the outer balloon is immediately adjacent to the outer surface of the inner balloon. The two surfaces are permitted to move with respect to each other. The outer balloon 8 is sealed to the outer surface 4 of the catheter shaft 2 at the ends of the balloon. The outer balloon 8 may be formed of a non-compliant material. In the illustrated embodiment, the length of the outer balloon is chosen so that it is approximately 4 mm longer than the stent. In this and other embodiments, when the stent is crimped around the deflated balloon, the same amount of balloon may extend past the stent on each side—i.e. the balloon may, for example, extend past the stent by 2 mm on each side.

An inflation lumen 16 is located within the catheter shaft 4. The inflation lumen 16 is in fluid communication with the interior 20 of the inner balloon 6 through an aperture 18 in the catheter shaft 4. A pressurized medium, such as saline, may be introduced into the inflation lumen 16 to inflate the inner balloon. The space between the inner balloon and the outer balloon is not provided with an inflation lumen.

Figure 2:
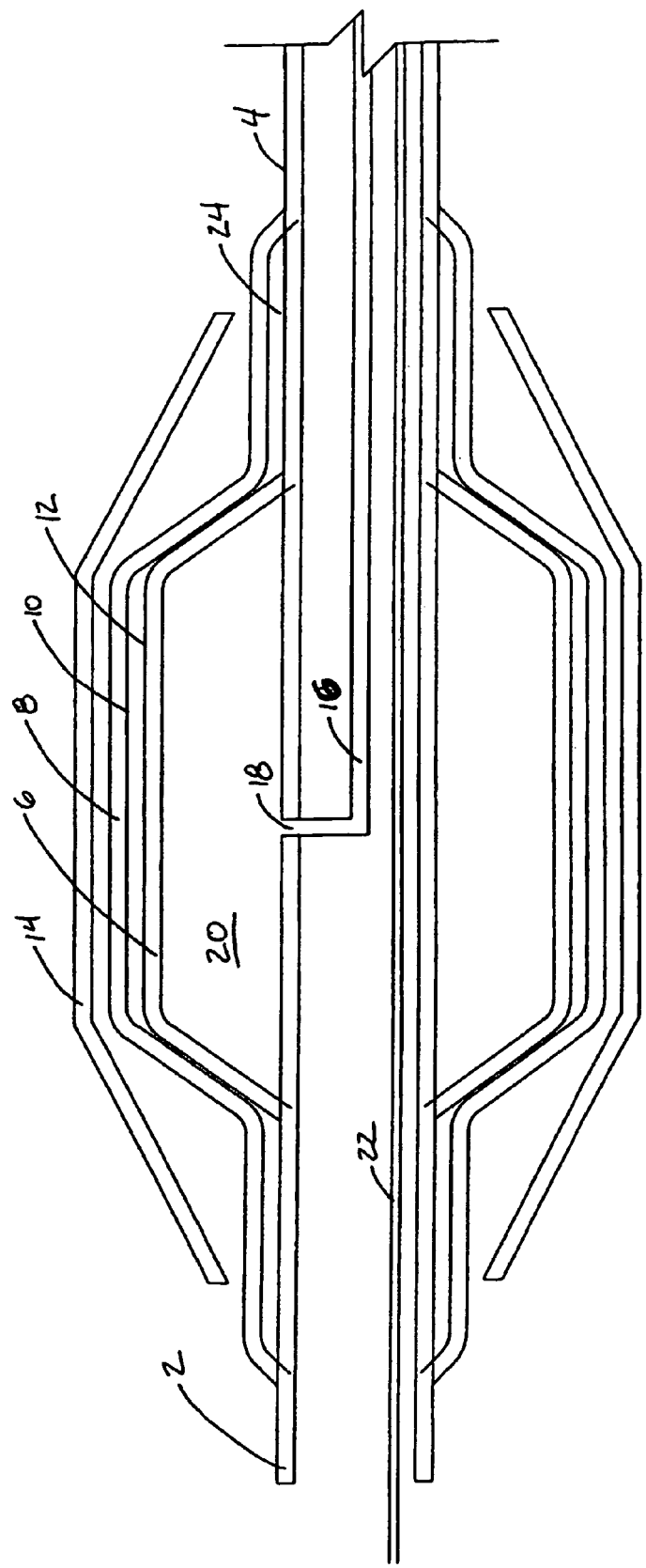
FIG. 2 shows a cross-sectional view of the catheter of FIG. 1 after partial inflation.

In operation, a guidewire 22 may be routed to the desired inflation location. The balloon catheter, the catheter shaft 4 of which has a guidewire port located adjacent the balloons, with a crimped stent may be then placed over the guidewire 22 and delivered to the desired location. A pressurized medium is introduced into the inflation lumen. The pressurized medium passes into the interior 20 of the inner balloon 6, and begins to inflate the inner balloon 6. The inner balloon 6 applies pressure to both the stent 14 and the outer balloon 8. Typically, at approximately 3 or 4 atmospheres (depending on the particular stent design chosen), the stent 14 begins to expand. As shown in FIG. 2, because the inner balloon 6 is shorter than the stent 14, only the middle portion of the stent 14 begins to expand. At, for example, approximately five atmospheres, the stent 14 is sufficiently expanded so that it is implanted into the vessel wall.

Figure 3:
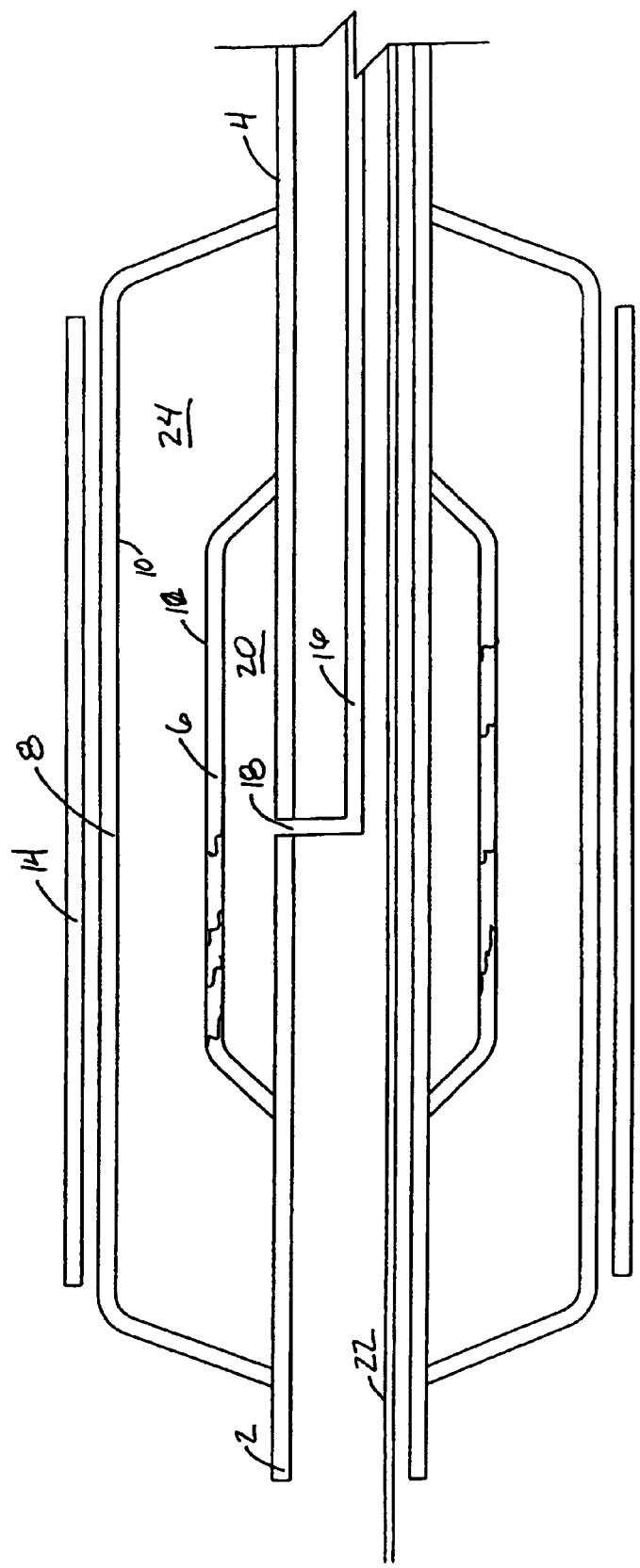
FIG. 3 shows a cross-sectional view of the catheter of FIG. 1 after full inflation.

As shown in FIG. 3, upon further application of the pressurized medium to the inflation lumen, the inner balloon 6 ruptures. The burst pressure of the inner balloon may be less than 10 atmospheres, and in some embodiments be approximately 5 atmospheres, for example. Rupture of the inner balloon 6 allows fluid communication between the inflation lumen 16 and the cavity formed between the outer balloon and the inner balloon.

When further pressure is applied to the inflation lumen, the outer balloon expands the entire length of the stent. The operator may then apply as much pressure as desired, up to the burst pressure of the outer balloon to firmly implant the stent. Typically, the burst pressure of the outer balloon should be greater than that of the inner balloon. Thus, for example, in a particular embodiment the burst pressure of the inner balloon may be selected to be, for example, 5 atmospheres, and the burst pressure of the outer balloon may be selected to be equal to 10 atmospheres, i.e., to give an approximately 5 atmosphere difference.

The balloons may then be deflated, and the catheter and guidewire may then by removed.

In the foregoing specification, the invention has been described with reference to specific exemplary embodiments. It will, however, be evident that various modifications and changes may be made thereunto without departing from the broader spirit and scope of the invention as set forth in the appended claims. The specification and drawings are accordingly to be regarded in an illustrative rather than a restrictive sense.

What is claimed is:

1. A stent and balloon catheter in combination comprising:
   a balloon catheter with an inner and an outer balloon, the outer balloon overlaying the inner balloon; and
   an expandable stent mounted over the inner and outer catheter balloons,
   wherein:
   a burst pressure of the inner balloon is less than a burst pressure of the outer balloon, a length of the outer balloon is greater than a length of the stent and a length of the inner balloon is less than the length of the stent; and
   the burst pressure of said inner balloon being such that, when inflated with a pressurized medium it will expand sufficiently to expand the middle portion of said stent and implant said stent.

2. A balloon catheter according to claim 1 wherein the burst pressure of the inner balloon is less than 10 atmospheres.

3. A balloon catheter according to claim 2 wherein the burst pressure of the inner balloon is approximately 5 atmospheres.

4. A balloon catheter according to claim 3 wherein the burst pressure of the outer balloon is greater than 10 atmospheres.

5. A balloon catheter according to claim 3 wherein the outer balloon is formed of a non-compliant material.

6. A balloon catheter according to claim 5 wherein the inner balloon is formed of a non-compliant material.

7. A balloon catheter according to claim 1 wherein the burst pressure of the inner balloon is approximately 5 atmospheres.

8. A balloon catheter according to claim 1 wherein the burst pressure of the outer balloon is greater than 10 atmospheres.

9. A balloon catheter according to claim 1 wherein the outer balloon is formed of a non-compliant material.

10. A balloon catheter according to claim 9 wherein the inner balloon is formed of a non-compliant material.

11. A balloon catheter according to claim 1 wherein the catheter shaft has a guidewire port located adjacent the balloons.

12. A balloon catheter according to claim 1 wherein the burst pressure of the first balloon is at least 5 atmospheres less than the burst pressure of the second balloon.

13. A balloon catheter according to claim 1 wherein the burst pressure of said outer balloon is such that, when inflated with a pressurized medium it will expand sufficiently to expand the entire length of the stent.

14. A stent and balloon catheter in combination comprising:
   a balloon catheter with an inner and an outer balloon, the outer balloon overlaying the inner balloon, both said inner balloon and said outer balloon sealed to a catheter shaft at each end;
   an inflation lumen in said catheter shaft in communication only with an interior of said inner balloon; and
   an expandable stent mounted over the first and second catheter balloons,
   wherein:
   a burst pressure of the inner balloon is less than a burst pressure of the outer balloon, a length of the outer balloon is greater than a length of the stent and a length of the inner balloon is less than the length of the stent;
   the burst pressure of said inner balloon is such that, when inflated with a pressurized medium from said inflation lumen, it will expand sufficiently to expand the middle portion of said stent and implant said stent, before bursting; and
   pressurized medium from said inflation lumen can enter the interior of said outer balloon to inflate it and further expand the stent over its full length only after said inner balloon bursts.

15. A balloon catheter according to claim 14 wherein the burst pressure of the inner balloon is less than 10 atmospheres.

16. A balloon catheter according to claim 15 wherein the burst pressure of the inner balloon is approximately 5 atmospheres.

17. A balloon catheter according to claim 16 wherein the burst pressure of the outer balloon is greater than 10 atmospheres.

18. A balloon catheter according to claim 15 wherein the outer balloon is formed of a non-compliant material.

19. A balloon catheter according to claim 18 wherein the inner balloon is formed of a non-compliant material.

20. A balloon catheter according to claim 14 wherein the outer balloon is formed of a non-compliant material.

21. A balloon catheter according to claim 20 wherein the inner balloon is formed of a non-compliant material.

22. A balloon catheter according to claim 14 wherein the catheter shaft has a guidewire port located adjacent the balloons.

23. A balloon catheter according to claim 14 wherein the burst pressure of the first balloon is at least 5 atmospheres less than the burst pressure of the second balloon.

* * * * *